US00PP22506P3

(12) United States Plant Patent
Pierron-Darbonne

(10) Patent No.: US PP22,506 P3
(45) Date of Patent: Feb. 21, 2012

(54) STRAWBERRY PLANT NAMED 'SABRINA'

(50) Latin Name: *Fragaria×ananassa*
Varietal Denomination: SABRINA

(75) Inventor: Alexandre Pierron-Darbonne, Pamplona (ES)

(73) Assignee: Plantas De Navarra, S.A., Valtierra, Navarra (ES)

( * ) Notice: Subject to any disclaimer, the term of this patent is extended or adjusted under 35 U.S.C. 154(b) by 0 days.

(21) Appl. No.: 12/802,297

(22) Filed: Jun. 2, 2010

(65) Prior Publication Data

US 2010/0313317 P1 Dec. 9, 2010

(30) Foreign Application Priority Data

Jun. 3, 2009 (QZ) ..... PBR 2009/1037

(51) Int. Cl.
*A01H 5/00* (2006.01)

(52) U.S. Cl. ..... Plt./208

(58) Field of Classification Search ..... Plt./208
See application file for complete search history.

*Primary Examiner* — June Hwu

(74) *Attorney, Agent, or Firm* — Christie, Parker & Hale, LLP

(57) ABSTRACT

The present invention relates to a new and distinct strawberry variety. The varietal denomination of the new variety is 'SABRINA'. Among the characteristics which appear to distinguish the new variety from other varieties are a combination of traits which include inflorescence that appears level with the foliage, same size of calyx relative to corolla and abundant production of red colored, conical shaped, and firm fruit, large fruit size, and medium time of ripening.

15 Drawing Sheets

Botanical classification: *Fragaria×ananassa* 'SABRINA'.

Varietal denomination: The new plant has the varietal denomination Duch.

BACKGROUND OF THE INVENTION

The new variety of strawberry was created in a breeding program by crossing two parents; in particular, by crossing as seed parent an undistributed strawberry parent designated 9719 (unpatented) and as pollen parent an undistributed strawberry parent designated 94-020 (unpatented). Female and male are selections from breeder's program of Planasa. Both parental varieties are property and have not been commercialized.

The resulting seedling of the new variety was grown and asexually propagated by runners in Segovia, Spain, 3° 59'W., 41° 22'N., 2742 feet elevation. Clones of the new variety were further asexually propagated and extensively tested. This propagation and testing has demonstrated that the combination of traits disclosed herein which characterize the new variety are fixed and retained true to type through successive generations of asexual reproduction.

In seed parent 9719 (unpatented) the fruit size is smaller than in the new variety 'SABRINA'. In seed parent 9719 (unpatented) the terminal leaflet is as long as broad and shows a base shape obtuse, whereas in the new variety 'SABRINA' the terminal leaflet is longer than broad and shows a shape of base acute. Attitude of the calyx segments in the fruit of seed parent 9719 (unpatented) is reflexed, whereas in the new variety 'SABRINA' is spreading. Plant of pollen parent 94-020 (unpatented) is less vigorous than the plant of the new variety 'SABRINA'. In pollen parent 94-020 (unpatented) the position of the inflorescence relative to the foliage is above, whereas in the new variety 'SABRINA' is level with the foliage. In pollen parent 94-020 (unpatented) the fruit size is smaller than in the new variety 'SABRINA'.

SUMMARY OF THE INVENTION

The present invention relates to a new and distinct strawberry variety. The varietal denomination of the new variety is 'SABRINA'. Among the characteristics which appear to distinguish the new variety from other varieties are a combination of traits which include inflorescence that appears level with the foliage, same size of calyx relative to corolla and abundant production of red colored, conical shaped, and firm fruit, large fruit size, and medium time of ripening (50% of plants with ripe fruits).

COMPARISON TO CLOSEST VARIETY

The new variety is closest to the variety 'Sabrosa' (U.S. Plant Pat. No. 16,558) and the variety 'Camarosa' (U.S. Plant Pat. No. 8,708), but is distinguished therefrom by the following characteristics possessed by 'Sabrina' which are different than, or not possessed by, 'Sabrosa' (U.S. Plant Pat. No. 16,558) or 'Camarosa' (U.S. Plant Pat. No. 8,708).

1. Terminal leaflet in 'Sabrosa' (U.S. Plant Pat. No. 16,558) and 'Camarosa' (U.S. Plant Pat. No. 8,708) is as long as broad and shows a shape of base obtuse, than in 'Sabrina' is longer than broad and shows a shape of base acute.
2. Size of calyx relative to corolla in the flower of 'Camarosa' (U.S. Plant Pat. No. 8,708) is larger, than in 'Sabrina' is same size.
3. Length / width ratio of petal in 'Camarosa' (U.S. Plant Pat. No. 8,708) is as long as broad whereas Length / width ratio in 'Sabrina' is slightly broader than long.

4. Predominant fruit shape in 'Camarosa' (U.S. Plant Pat. No. 8,708) is wedged, then in 'Sabrina' the predominant fruit shape is conical.
5. 'Camarosa' (U.S. Plant Pat. No. 8,708) shows a dark red fruit color (RHS red group near 47 B to 47A), whereas in 'Sabrina' it is a red fruit color (RHS red group near 43 B to 43 A).
6. Size of calyx in relation to fruit diameter in 'Camarosa' (U.S. Plant Pat. No. 8,708) is slightly larger, than in the fruit of 'Sabrina' is slightly smaller.
7. Color of flesh in fruits of 'Camarosa' (U.S. Plant Pat. No. 8,708) (RHS red group near 42 A) is darker than color of flesh in fruits of 'Sabrina' (RHS red group near 41 B to 41 A).
8. Fruits of 'Camarosa' (U.S. Plant Pat. No. 8,708) show a hollow center weakly expressed, whereas in fruits of 'Sabrina' the hollow center is absent.
9. The fruit size in 'Sabrosa' (U.S. Plant Pat. No. 16,558) is smaller than in 'Sabrina' one.
10. Attitude of the calyx segments in the fruit of 'Sabrosa' (U.S. Plant Pat. No. 16,558) is refluxed, than in the fruit of 'Sabrina' is spreading.
11. Color of flesh in fruits of Sabrosa (U.S. Plant Pat. No. 16,558) (RHS red group near 43 B) is darker than color of flesh in fruits of 'Sabrina' (RHS red group near 41 B to 41 A).

The differences in the length/width ratio and shape of base in the terminal leaflet of 'Sabrina' (designated 03.40.181) and 'Camarosa' (U.S. Plant Pat. No. 8,708) and 'Sabrosa' (U.S. Plant Pat. No. 16,558) are shown in FIG. 7 and FIG. 8 respectively. The differences in the size of calyx relative to corolla and in the length / width ratio of petal of the flowers of 'Sabrosa' (designated 03.40.181) and 'Camarosa' (U.S, Plant Pat. No. 8,708) are shown in FIG. 10 and FIG. 11 respectively. The differences in the fruits of 'Sabrina' (designated 03.40.181) and 'Camarosa' (U.S. Plant Pat. No. 8,708) are shown in FIG. 13 and FIG. 14. The differences in the fruits of 'Sabrina' (designated 03.40.181) and "Sabrosa" (U.S. Plant Pat. No. 16,558) are shown in FIG. 15. These differences are maintained during the harvest season.

BRIEF DESCRIPTION OF ILLUSTRATIONS

The accompanying photographs show typical specimens of the new variety, designated 03.40.181 in the illustrations, including fruit, foliage and flower, in color as nearly true as it is reasonably possible to make in color illustrations of this character.

The plants depicted in the drawings were planted Oct. 10, 2009 in the farm of La Mogalla in Cartaya (Huelva), Spain, about 7° W, 37° N, 45 feet elevation.

Drawings were taken March-April, 2010 (about March 25 and Apr. 8, 2010): minimum temperate about 10 to 12° Centigrade, maximum temperate about 22 to 24° Centigrade.

FIG. 1 shows several plants of the new variety (designated 03.40.181) which exhibit a plant dense and the position of the inflorescence relative to foliage is level with.

Figure 1:
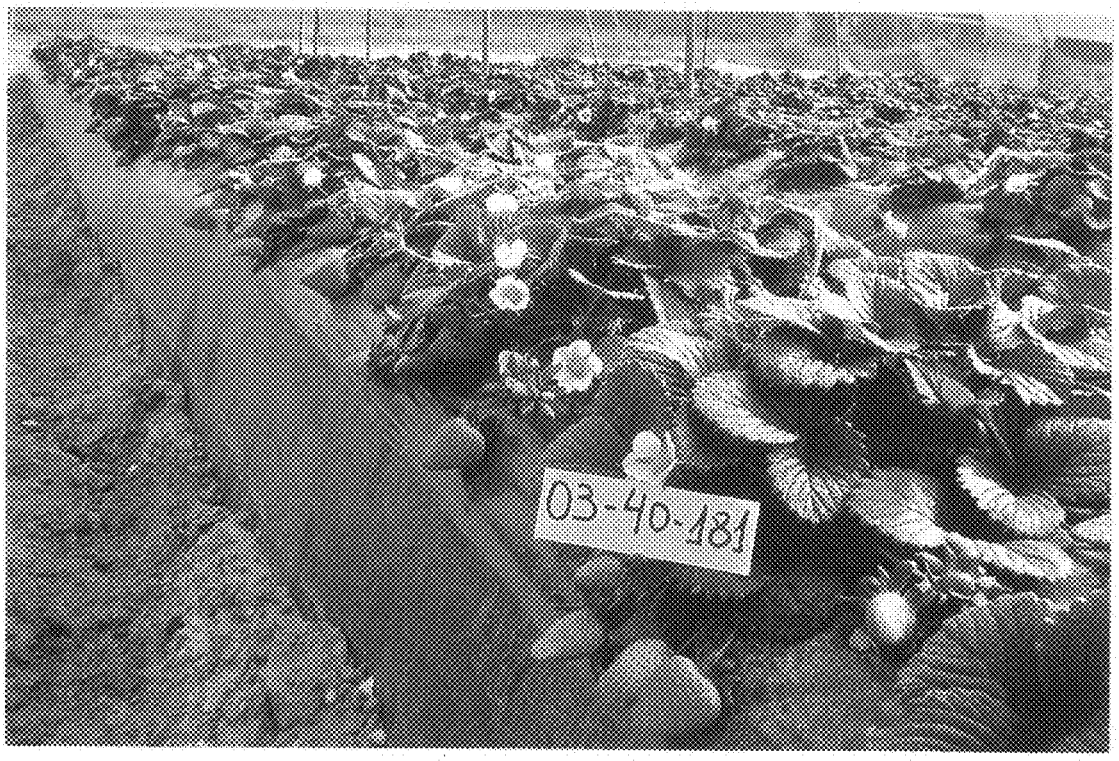
Figure 2:
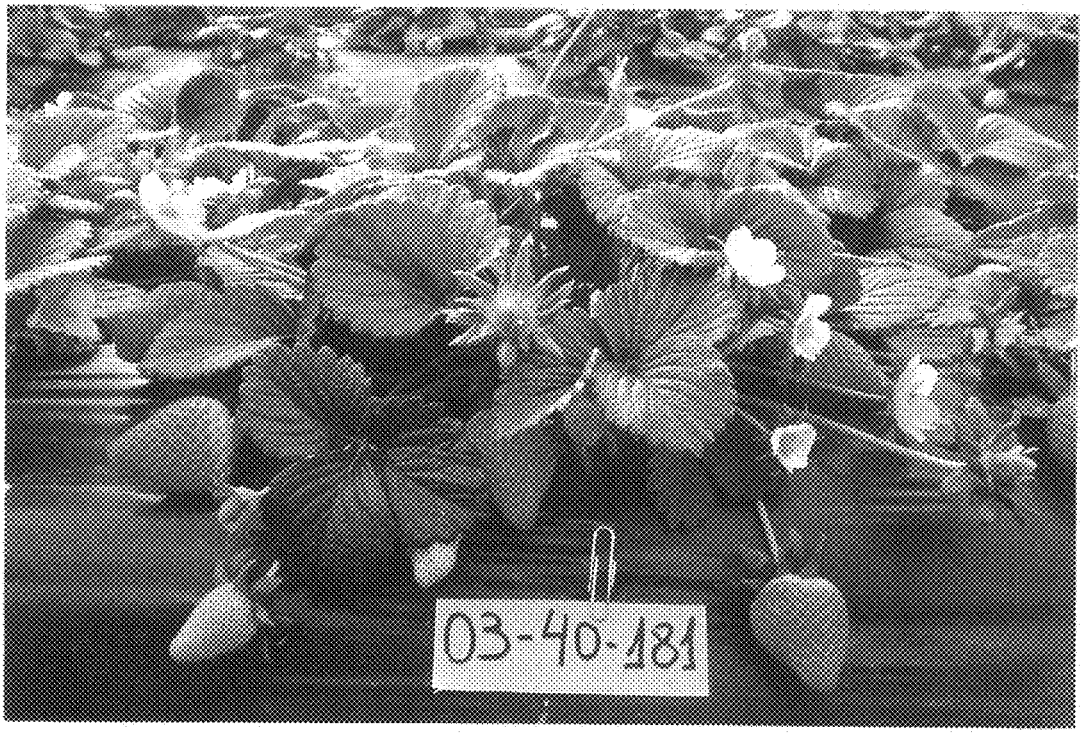
FIG. 2 shows several plants of the new variety (designated 03.40.181) with several red colored and conical shape fruits.
Figure 3:
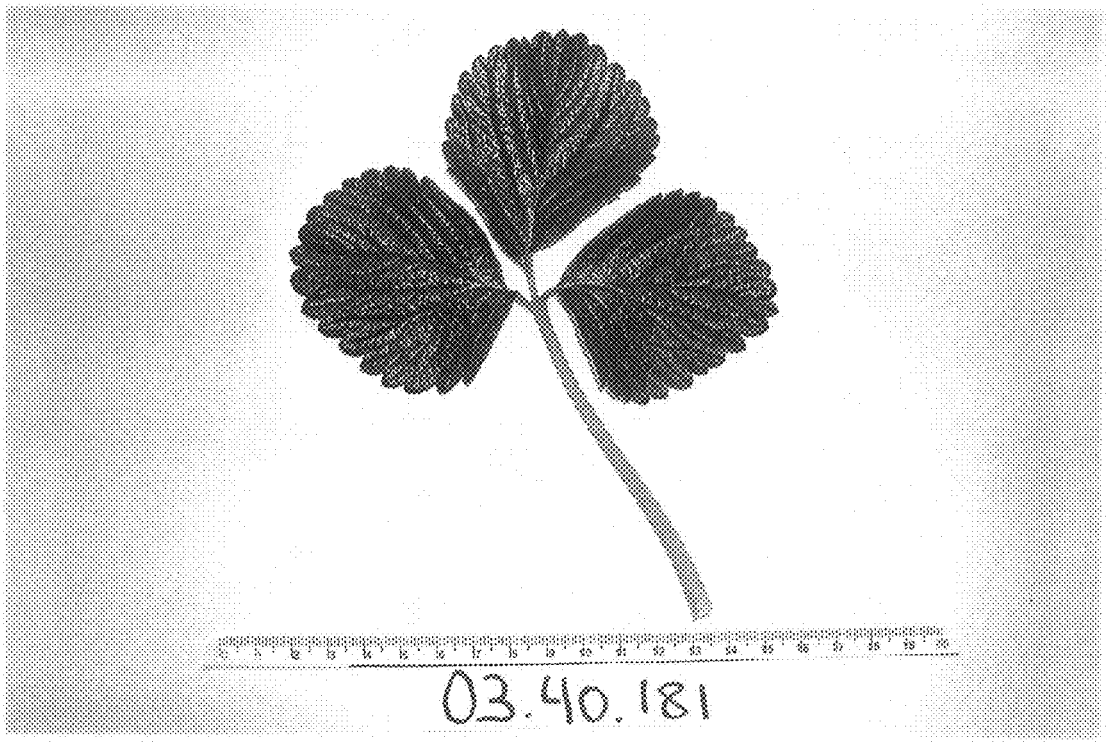
Figure 4:
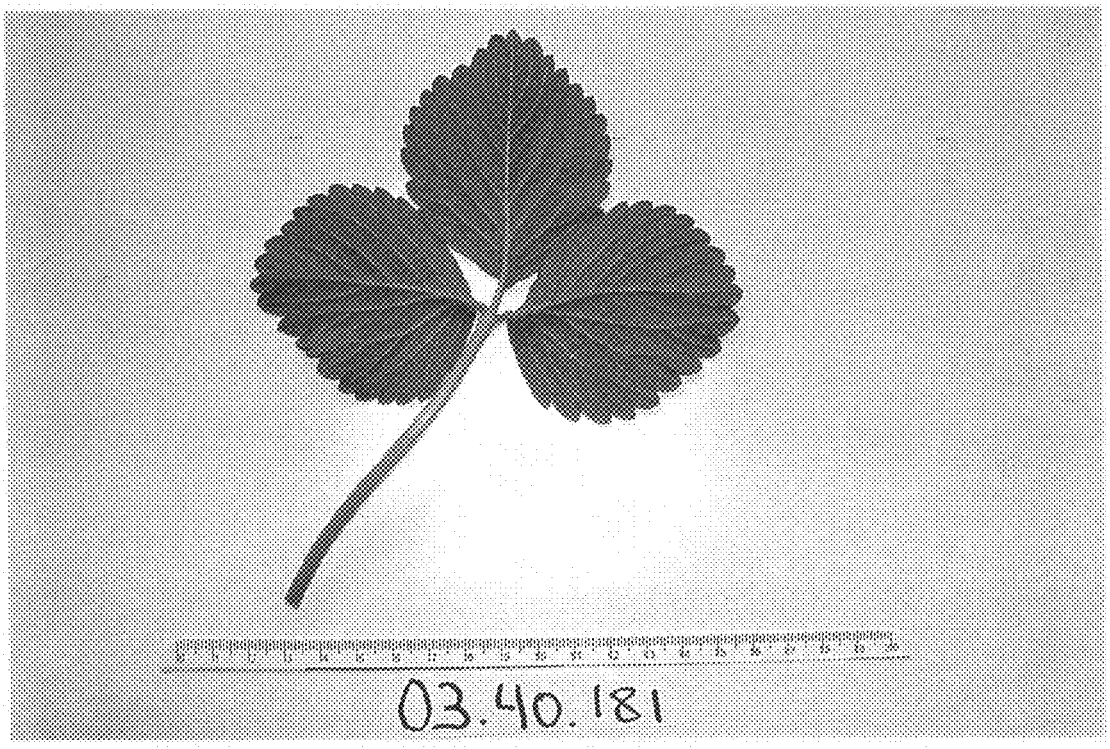

FIG. 3 and FIG. 4 show the upper side and the underside, respectively, of a complete leave of the new variety (designated 03.40.181). In it we can see that the leaf color of upper side of the new variety (designated 03.40.181) is RHS green group color (near 133A to 136 A) and the leaf color of underside of the new variety (designated 03.40.181) is RHS green group color (near 138 B to 138 A).

Figure 5:
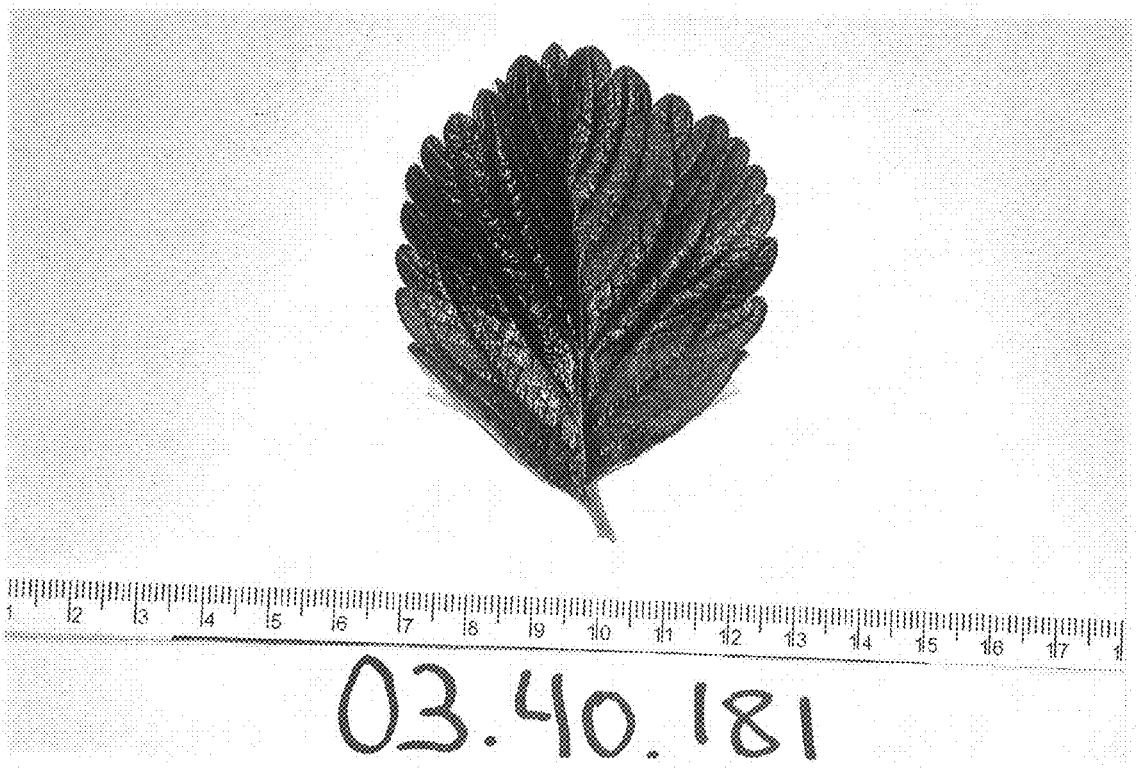
Figure 6:
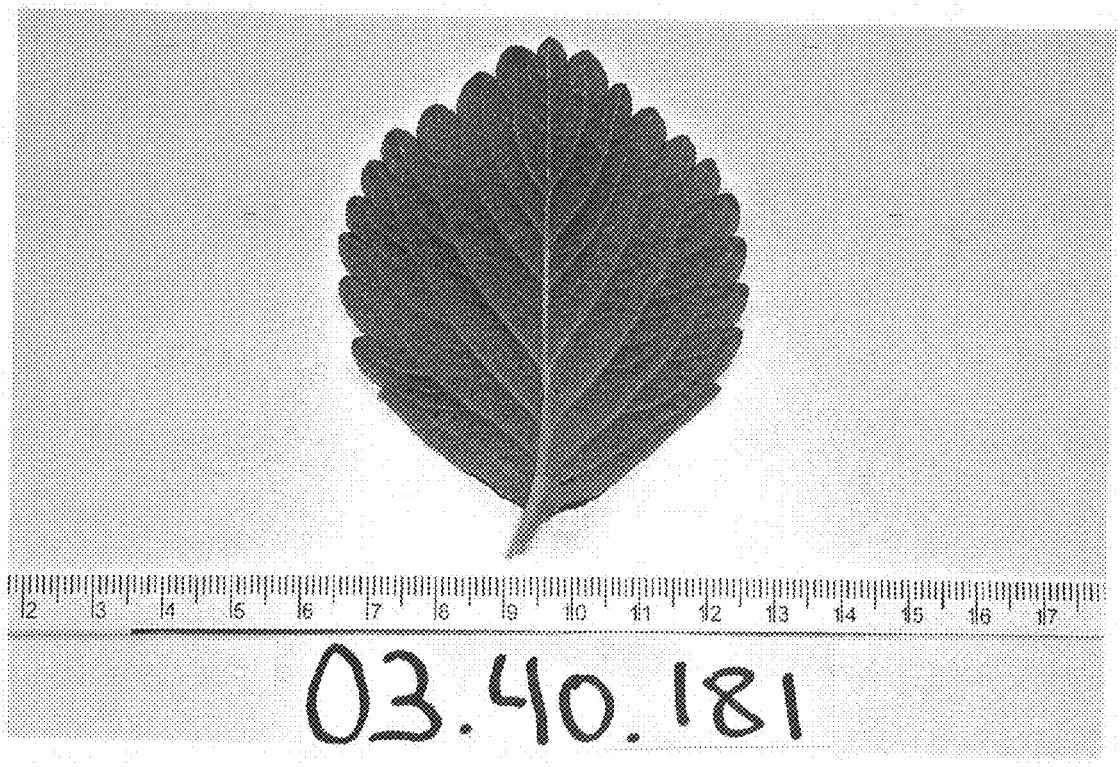

FIG. 5 and FIG. 6 show the upper side and the underside, respectively, of terminal leaflet of the new variety (designated 03.40.181). In it we can see that the leaf color of upper side of the new variety (designated 03.40.181) is RHS green group color (near 133 A to 136 A) and the leaf color of underside of the new variety (designated 03.40.181) is RHS green group color (near 138 B to 138 A).

Figure 7:
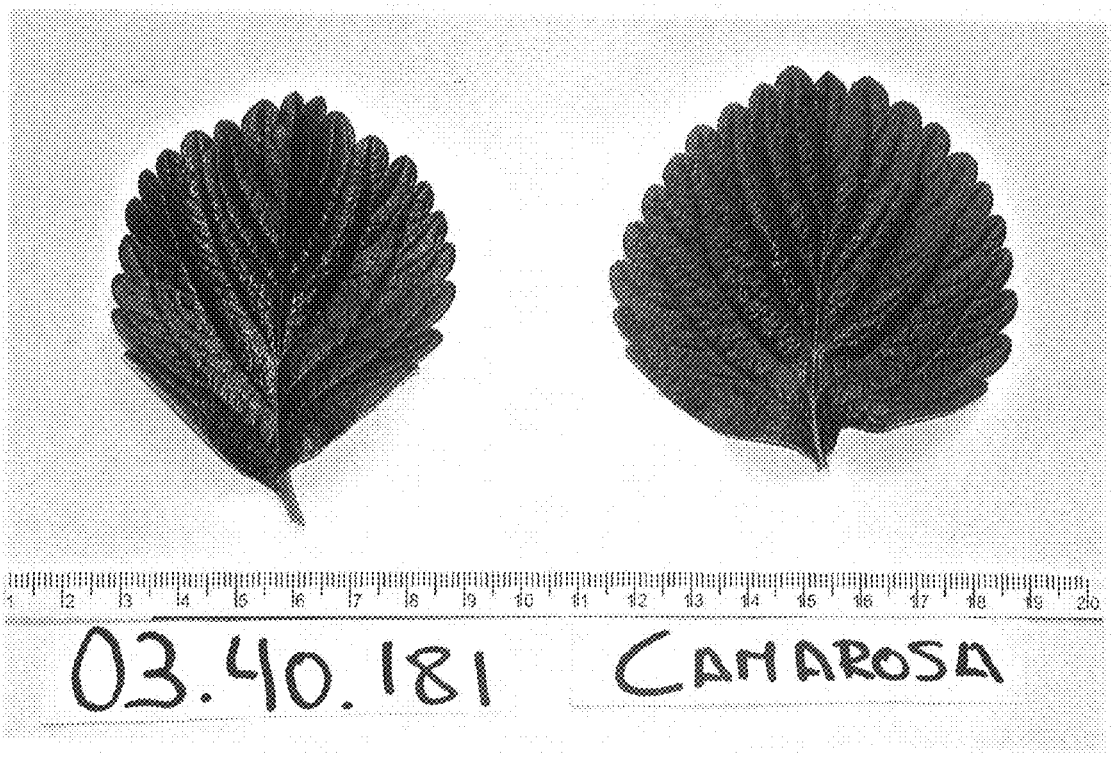

FIG. 7 shows the terminal leaflet of strawberry variety 'Camarosa' (U.S. Plant Pat. No. 8,708) in comparison with the terminal leaflet of the new variety (designated 03.40.181). We can appreciate that the terminal leaflet in strawberry variety 'Camarosa' (U.S. Plant Pat. No. 8,708) is as long as broad and shows a shape of base obtuse, than in the new variety (designated 03.40.181) the terminal leaflet is longer than broad and shows a shape of base acute.

Figure 8:
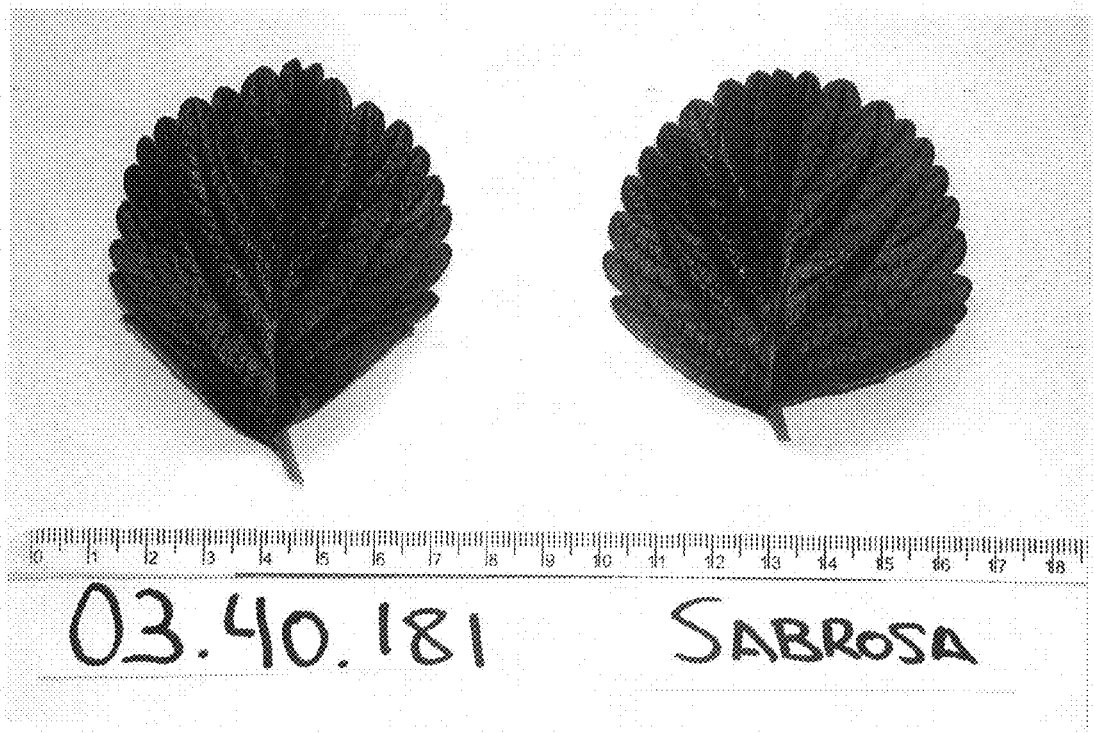

FIG. 8 shows the terminal leaflet of strawberry variety 'Sabrosa' (U.S. Plant Pat. No. 16,558) in comparison with the terminal leaflet of the new variety (designated 03.40.181). We can appreciate that the terminal leaflet in strawberry variety 'Sabrosa' (U.S. Plant Pat. No. 16,558) is as long as broad and shows a shape of base obtuse, than in the new variety (designated 03.40.181) the terminal leaflet is longer than broad and shows a shape of base acute.

Figure 9:
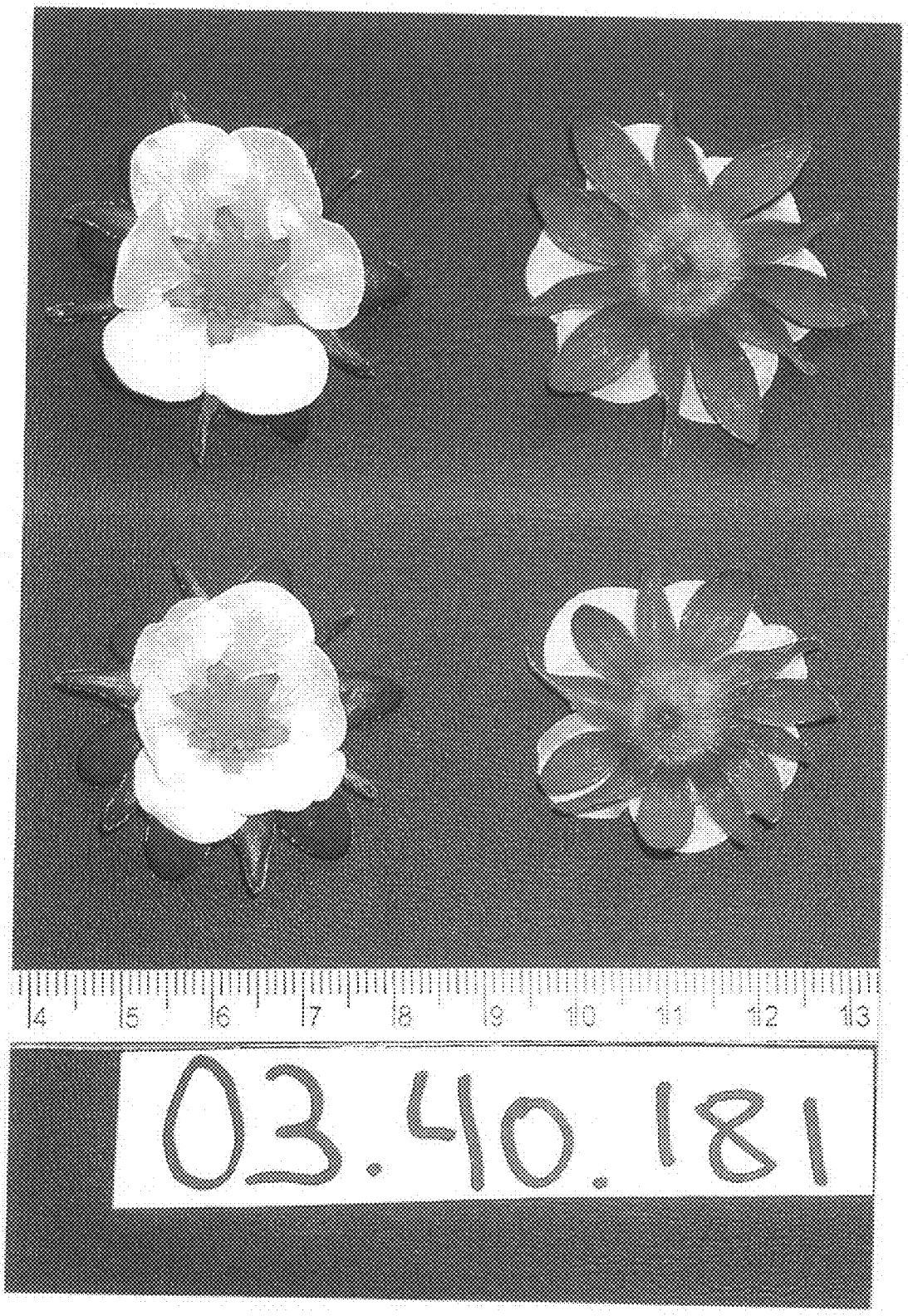

FIG. 9 shows the flower of the new variety (designated 03.40.181).

Figure 10:
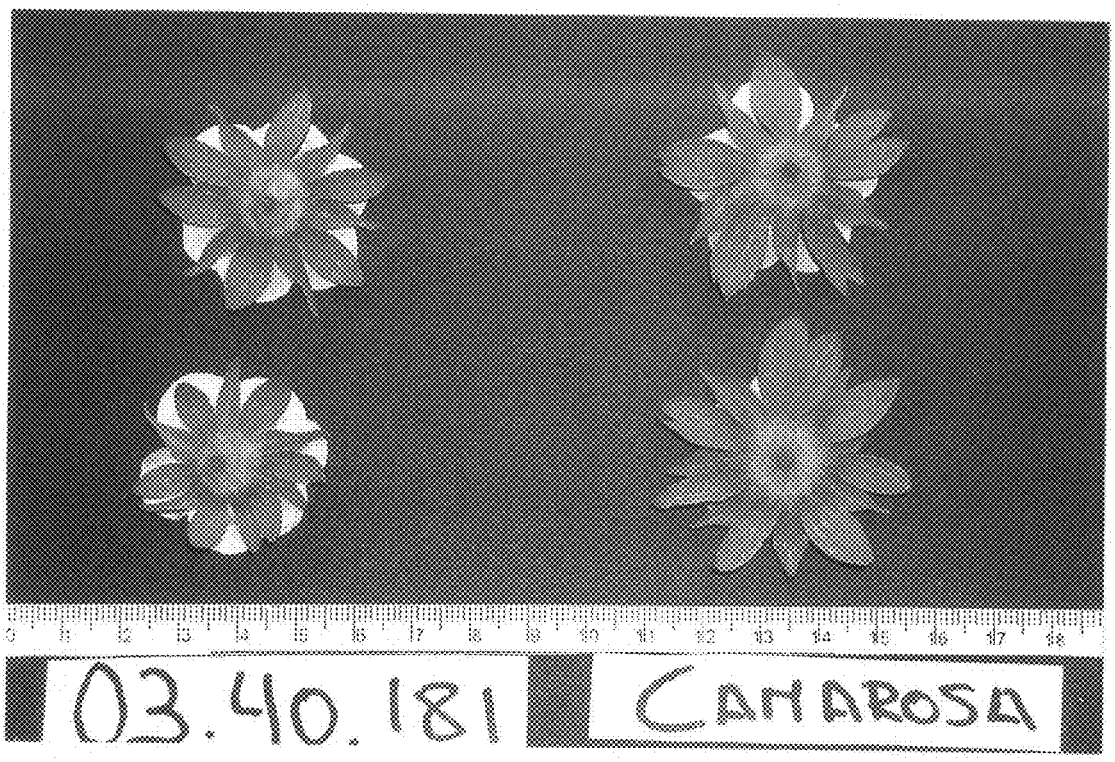

FIG. 10 shows that the size of calyx relative to corolla in the flower of strawberry variety 'Camarosa' (U.S. Plant Pat. No. 8,708) is larger whereas the size of calyx relative to corolla in the flower of the new variety (designated 03.40.181) is same size.

Figure 11:
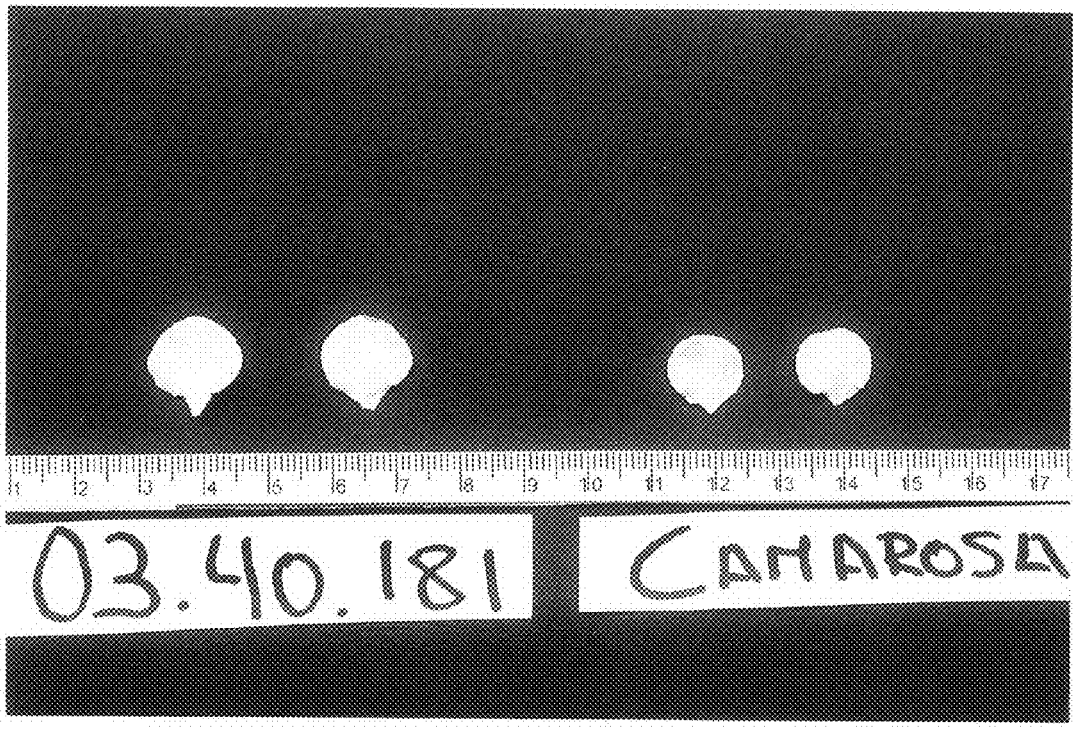

FIG. 11 shows the comparison of length / width ratio of petals of strawberry variety 'Camarosa' (U.S. Plant Pat. No. 8,708), as long as broad, and of petals of the new variety (designated 03.40.181), slightly broader than long.

Figure 12:
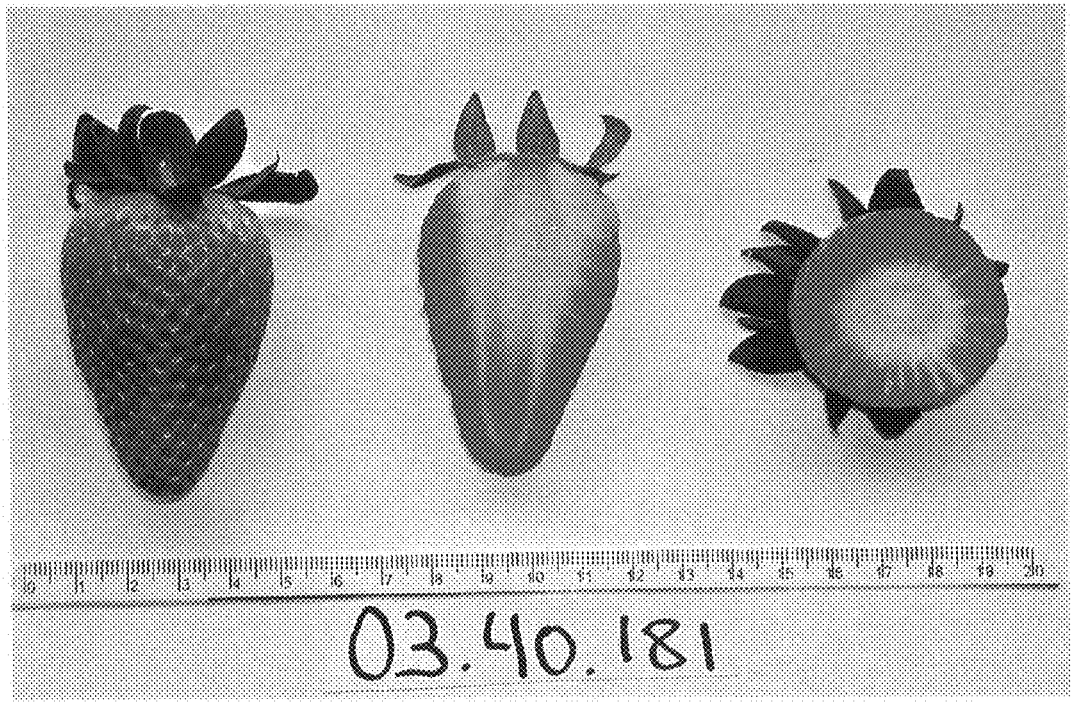

FIG. 12 shows typical fruit of the new variety (designated 03.40.181) whole, sliced and in cross section, illustrating the typical flesh coloration (RHS red group near 41 B to 41 A), with an absent hollow center, conical shape and red fruit color (RHS red group near 43 B to 43 A).

Figure 13:
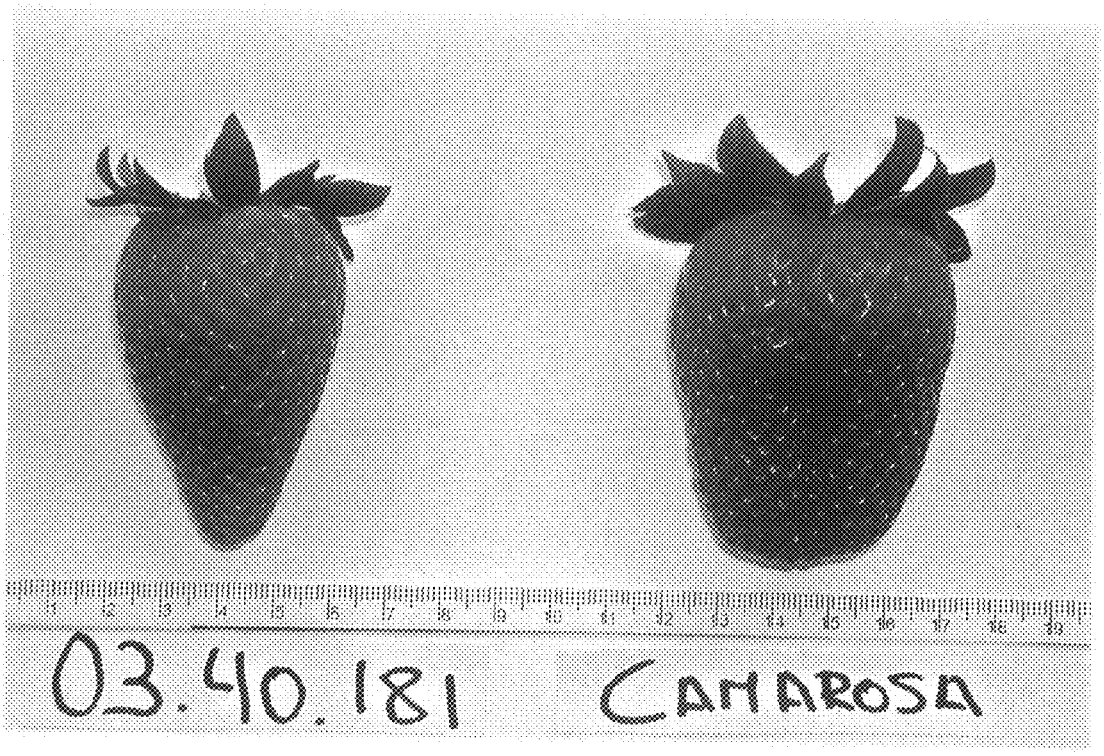

FIG. 13 shows the comparison between fruits of the new variety (designated 03.40.181) and the strawberry variety 'Camarosa' (U.S. Plant Pat. No. 8,708). In it we can see that the fruit shape of the strawberry variety 'Camarosa' (U.S. Plant Pat. No. 8,708) is wedged whereas in the new variety (designated 03.40.181) is conical and the fruits of the strawberry variety 'Camarosa' (U.S. Plant Pat. No. 8,708) show a dark red fruit color (RHS red group near 47 B to 47A), whereas in the new variety (designated 03.40.181) the fruits show a red fruit color (RHS red group near 43 B to 43 A).

Figure 14:
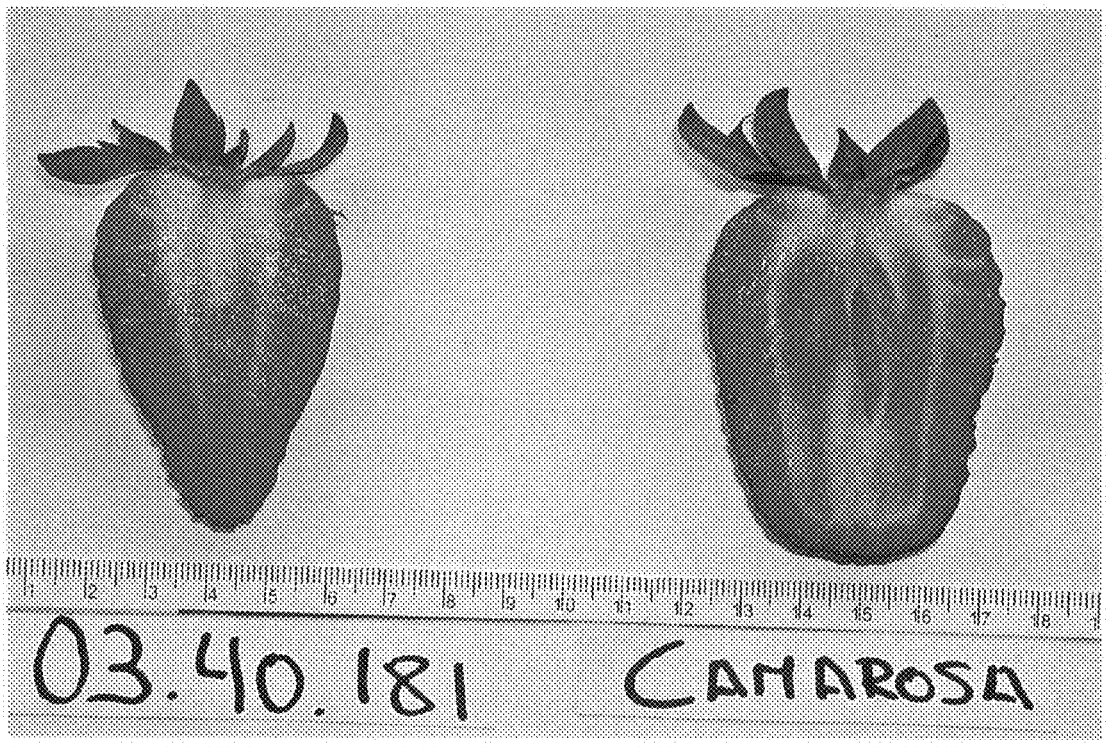

FIG. 14 shows the comparison between fruits of the new variety (designated 03.40.181) and the strawberry variety 'Camarosa' (U.S. Plant Pat. No. 8,708). In it we can see that the fruit color of flesh in fruits of the strawberry variety 'Camarosa' (U.S. Plant Pat. No. 8,708) (RHS red group near 42 A) is darker than color of flesh in fruits of the new variety (designated 03.40.181) (RHS red group near 41 B to 41 A), and the fruits of the strawberry variety 'Camarosa' (U.S. Plant Pat. No. 8,708) show a hollow center weakly expressed, whereas in fruits of the new variety (designated 03.40.181) the hollow center is absent.

Figure 15:
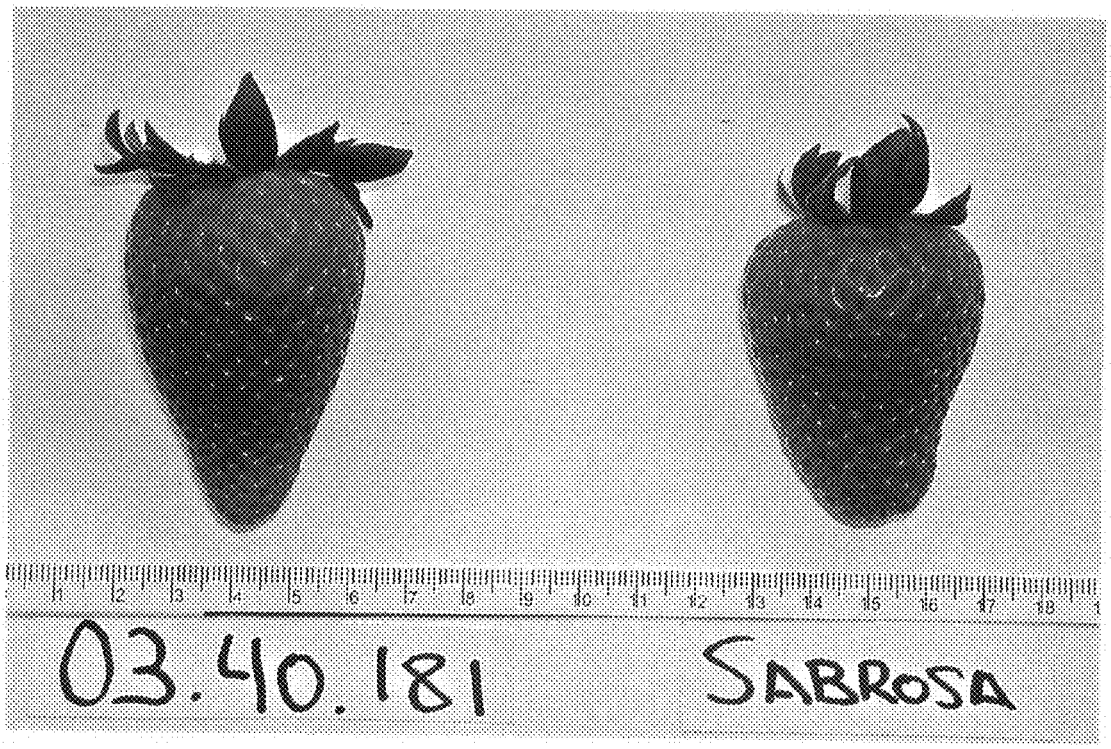

FIG. 15 shows the comparison between fruits of the new variety (designated 03.40.181) and the strawberry variety 'Sabrosa' (U.S. Plant Pat. No. 16,558). In it we can see that the fruit size in the strawberry variety 'Sabrosa' (U.S. Plant Pat. No. 16,558) is smaller than in the new variety (designated 03.40.181), and the attitude of the calyx segments in the fruit of the strawberry variety 'Sabrosa' (U.S. Plant Pat. No. 16,558) is reflexed, than in the fruit of the new variety (designated 03.40.181) is spreading.

DESCRIPTION OF THE NEW VARIETY

The following detailed description of the new variety is based upon observations taken of plants and fruits grown "underglass", i.e. undertunnel, in the farm of La Mogalla in Cartaya (Huelva), Spain, 7° W., 37° N., 45 feet elevation.

The following description is in accordance with UPOV terminology and the color terminology herein is in accordance with The Royal Horticultural Society Colour Chart (R.H.S.C.C.), Third Edition, published in 1995. The color descriptions and other phenotypical descriptions may deviate from the stated values and descriptions depending upon variation in environmental, seasonal, climatic and cultural conditions.

PROPAGATION

The new variety is principally propagated by way of runners. Although propagation by runners is presently preferred, other know methods of propagating strawberry plants may be used. Strawberries root well after transplanting.

The term "blistering" used herein refers to the texture or rugosity or surface ondulation inherent to leaves and is generally a constant characteristic.

GENERAL

'Sabrina' is a short day variety that needs an induction to flowering by chilling, such as occurs at a high elevation nursery (fresh plant) or with cold storage (referred to as a frigo). Usually a short time is sufficient. 'Sabrina' is self-fertile. It produces large quantity of pollen throughout the seasons and pollination is generally good as there are very few malformed fruit.

Production: Plants described are from high elevation nursery.

Trials pursued in Cartaya (Huelva), Spain.

*Date of planting.*—11th Oct., 2008.

*Number of repetitions.*—2.

*Plants per repetition.*—225.

TABLE 1

Accumulated production of 1st quality fruit (g/plant)

| Variety | 21 February | 28 March | 25 April | 15 May |
|---|---|---|---|---|
| SABRINA | 30 | 320 | 1012 | 1173 |
| SABROSA | 33 | 250 | 732 | 962 |
| CAMAROSA | 34 | 144 | 470 | 793 |

TABLE 2

Total Yield and fruit weight average

| Variety | 1st + 2nd Quality Fruit | Total | Weight (g/fruit) |
|---|---|---|---|
| SABRINA | 1173 + 439 | 1612 | 26-24 |
| SABROSA | 962 + 116 | 1078 | 23-22 |
| CAMAROSA | 793 + 437 | 1230 | 25-23 |

TABLE 3

Production total, to 15 May, of First Quality Fruit ($1^{st}$ quality) and Second Quality Fruit ($2^{nd}$ quality) in g/plant

| Variety | $1^{st}$ quality | $2^{nd}$ quality | TOTAL ($1^{st}$ quality + $2^{nd}$ quality) | % $2^{nd}$ quality |
|---|---|---|---|---|
| SABRINA | 1173 | 439 | 1612 | 27 |
| SABROSA | 962 | 116 | 1078 | 11 |
| CAMAROSA | 793 | 437 | 1230 | 35 |

$$\%\ 2^{nd}\ \text{quality} = \frac{2^{nd}\ \text{quality}}{\text{TOTAL}} \times 100$$

TABLE 4

Weight (g/Fruit) at two dates: 28 March and 15 May

| WEIGHT (g/fruit) | 28 March | 15 May |
|---|---|---|
| SABRINA | 26 | 24 |
| SABROSA | 23 | 22 |
| CAMAROSA | 25 | 23 |

WEIGHT is shown as the average weight per fruit in First Quality Fruits.

TABLE 5

| | SABROSA | SABRINA (03.40.181) | CAMAROSA |
|---|---|---|---|
| Firmness (Kg) | 1.30 | 1.40 | 1.20 |
| Humidity & Volatile Matter (%) | 92.50 | 91.50 | 91.10 |
| Dry Matter (%) | 7.50 | 8.50 | 8.90 |
| PH (to 20°) | 3.60 | 3.60 | 3.60 |
| Acidity as Anhydride Citric (%) | 0.70 | 0.75 | 0.94 |
| Soluble Solids (°Brix) | 5.70 | 6.90 | 7.60 |
| Maturity Index | 8.10 | 9.20 | 8.10 |
| Content in Ascorbic Acid (mg/Kg) | 25 | 30 | 99.9 |
| Dominant Tonality(nm) | 500 | 500 | 510 |
| Luminosity: Transmittance to 460 nm | 44.30 | 50.00 | 36.40 |

The following definitions apply:

Firmness: It is the fruit's resistance to penetration measured in Kilograms (Kg). The measure given has been obtained by the penetrometer ROZE Mod. Arbelette, with a 50 $mm^2$ section head.

Dry Matter: It is the weight of the residual left from the trituration of the fruit after the drying process at a temperature of 103° C.±2° C. until reaching constant weight.

$$(\%)\ \text{Dry Matter} = \frac{\text{Weight Dry Matter}}{\text{Weight Fresh Matter}} \times 100$$

Humidity & Volatile Matter: Represents the content in volatile matters and water of the fruits.

$$(\%)\ \text{Humidity \& Volatile Matter} = 100 - \%\ \text{Dry Matter}$$

Maturity Index: Relation between Soluble solids and Acidity as Anhydride Citric.

$$\text{Maturity Index} = \frac{\text{Soluble solids}}{\text{Acidity as Anhydride Citric}}$$

The following additional information is provided to further describe the new variety.

Variety: Sabrina, Breeder Ref. 03.40.181

Classification: *Fragaria×ananassa* Duch.

Plant:

*Habit.*—Globose.

*Density.*—Dense.

*Vigor.*—Strong.

*Height.*—About 21 cm.

*Width.*—About 22 cm.

Leaf:

*Upperside.*—RHS green group color (near 135 A to 136 A).

*Underside.*—RHS green group color (near 138 B to 138 A).

*Length.*—About 9 cm.

*Width.*—About 15 cm.

*Cross section.*—Slightly concave.

*Leaf surface ondulation or blistering.*—Weak.

*Number of leaflets.*—Three only.

*Surface texture.*—The upper side of the leaf shows weak ondulations and the lower side of the leaf shows the veins weakly expressed.

Leaf stem characteristics:

*Color.*—RHS yellow-green group (near 146 D to 145 A).

*Position of hairs.*—Slightly outwards.

*Length.*—About 13 cm.

Terminal leaflet:

*Length/width ratio.*—Longer than broad.

*Length.*—About 7.5 cm.

*Width.*—About 8 cm.

*Shape of base.*—Acute.

*Shape of teeth.*—Crenate.

Petiole:

*Position of hairs.*—Slightly outwards.

*Length.*—About 13 cm.

*Texture.*—Surface of petiole shows a soft texture with few hairs slightly outwards oriented.

Stipule:

*Anthocyanin coloration.*—Absent or very weak.

*Color.*—RHS green group coloration (near 138D to 139 D).

*Average size.*—About 2.5 to 3.0 cm.

Stolons:

*Number.*—Medium, about 7.

*Thickness.*—Medium, about 3.5 mm.

*Pubescence.*—Medium.

*Color.*—RHS yellow-green group (near 146 D to 146 C).

*Length.*—About 20 cm.

Inflorescence:

*Position relative to foliage.*—Level with.

Flower:

*Size.*—Medium.

*Size of calyx relative to corolla.*—Same size.

*Spacing of petals.*—Overlapping.

Flower characteristics:

*Diameter primary flowers.*—About 3.5-3.9 cm.

*Diameter secondary flowers.*—About 3.0-3.5 cm.

*Number of petals.*—Normally about 6. No significant fragrance.

*Time from bloom to mature fruit (in Huelva, Spain).*—About 35 to 40 days.

*Stamens.*—Number per flower: about 22-26 with pollen present, fertile and abundant. Length — approximately 4 mm. Color — RHS white group to green-white group (near 155 D to 155 C and 157 D).

*Anthers.*—Generally average in size. Color — RHS yellow group (near 12 B to 13 B) and darkening with advanced maturity.

*Pollen.*—Fertile and abundant. Color — RHS yellow orange group (near 15 B to 15 C).

*Pistils.*—Number per flower: about 170-200, generally average in size. Color — RHS yellow group (near 12B to 13 B).

Petal:

*Length/width ratio.*—Broader than long. Length — Approximately 13 to 14 mm. Width — Approximately 19 to 20 mm. Shape — Slightly ovate. Colour — RHS white group (near 155 D to 155 C).

Fruiting truss:

*Attitude.*—Semi-erect.

Fruit:

*Ratio of length/maximum width.*—Slightly broader than long.

*Color.*—RHS red group (near 43 B to 43 A).

*Peduncle length of inflorescence stem.*—Primary fruit about 16 to 18 cm, secondary fruit about 12 to 13 cm, color RHS yellow-green group (near 146 D to 146 C).

Primary fruit:

*Length.*—About 5.5-6.0 cm.

*Width.*—About 4.0-4.5 cm.

Secondary fruit:

*Length.*—About 5.0-5.5 cm.

*Width.*—About 3.5-4.0 cm.

*Size.*—Large.

*Predominant shape.*—Conical.

*Difference in shapes between primary and secondary fruits.*—Slight.

*Band without achenes.*—Absent or very narrow.

*Color of achenes.*—RHS orange red group (near 32 C to 32 B).

*Unevenness of surface.*—Weak.

*Evenness of color.*—Even.

*Glossiness.*—Medium.

*Insertion of achenes.*—Below surface.

*Insertion of calyx.*—With fruit level.

*Pose of the calyx segments.*—Spreading.

*Size of calyx in relation to fruit diameter.*—Slightly smaller. The calyx presents 7 to 8 sepals with lanceolate shape and, in addition, 4 to 6 sepals smaller. All have a pointed shape.

*Colour upperside of sepals.*—Green group (near 135 B to 136 B). Colour underside of sepals — Green group (near 138 B to 138 A).

*Length of sepals.*—About 2.0 to 2.2 cm.

*Width of sepals.*—About 8 to 11 cm.

*Adherence of calyx.*—Strong.

*Firmness.*—Firm.

*Color of flesh.*—RHS red group (near 41 B to 41 A).

*Distribution of red color of flesh.*—Only marginal.

*Hollow center.*—Absent or very weakly expressed.

*Sweetness.*—Medium. 6.9 ° Brix.

*Acidity.*—Medium. 0,75% (Acidity as Anhydride Citric).

*Time of flowering* (50% *of plants at first flower*).—Medium.

*Time of ripening* (50% *of plants with ripe fruits*).—Medium.

*Type of bearing*.—Not remontant.

*Chilling*.—Weak.

*Planting date*.—Oct. 11, 2008.

10% *Flowering*.—Dec. 16, 2008.

*First mature fruits*.—Jan. 24, 2009.

*Maturity* (15-20 *gms/plant*).—Feb. 7, 2009.

Time of flowering data:

*Date of planting*.—Oct. 11, 2008 in the farm of La Mogalla, in Cartaya (Huelva), Spain, about 7° W, 37° N, 45 feet elevation. 10% flowering occurs about Dec. 16, 2008 with first mature fruit about Jan. 24, 2009 and maturity (15-20 g /plant) about Feb. 7, 2009.

*Time of flowers* (50% *of plants at first flower*).—About Dec. 26, 2008.

Storage qualities: 'Sabrina' fruit maintain their quality characteristics when keeping them in a frigo chamber at temperatures of about 2° C. during 48 hours. The fruit's color remains substantially the same.

Time of ripening: After planting as aforesaid, plants are grown in raised beds undertunnel (small tunnel with small holes in plastic walls). Water and fertilizer were applied through drip irrigation. Time of ripening (50% of plants with ripe fruit) is about Jan. 28, 2009. First mature fruit is about Jan. 24, 2009 and maturity (15-20 gmss/plant) is about Feb. 7, 2009.

General: The growing period in Huelva, Spain, where the observations were made, is between about December, 10 and May, 15 of each year, with a maximum production at about mid-April. 'Sabrina' is a short variety that benefits from induction to flowering by chilling, usually a few hours are sufficient, preferably at temperatures of 7° C. or less. Normally, the minimum number of hours is accumulated in the field during several days.

Disease resistance: No particular sensitivity to any disease or parasite has been observed for 'Sabrina'.

I claim:

1. A new and distinct strawberry plant of the variety substantially as shown and described.

* * * * *